United States Patent [19]

Cho

[11] 4,450,264
[45] May 22, 1984

[54] SILOXANE-CONTAINING POLYMERS AND CONTACT LENSES THEREFROM

[75] Inventor: Edward Cho, Westfield, N.J.

[73] Assignee: Polymatic Investment Corp., N.V., Curacao, Netherlands

[21] Appl. No.: 406,582

[22] Filed: Aug. 9, 1982

[51] Int. Cl.³ .................. C08F 30/08; C08F 130/08; C08F 230/08
[52] U.S. Cl. .................................. 526/279; 556/453
[58] Field of Search .................. 556/453; 526/279

[56] References Cited

U.S. PATENT DOCUMENTS

| | | | |
|---|---|---|---|
| 3,746,734 | 7/1973 | Berger et al. | 526/279 |
| 4,038,302 | 7/1977 | Reichel et al. | 556/453 |
| 4,139,513 | 5/1979 | Tanaka et al. | 526/279 |
| 4,153,641 | 5/1979 | Deickert et al. | 526/279 |
| 4,182,822 | 1/1980 | Chang | 526/279 |
| 4,303,772 | 12/1981 | Novicky | 526/279 |

*Primary Examiner*—Joseph L. Schofer
*Assistant Examiner*—Peter F. Kulkosky
*Attorney, Agent, or Firm*—Cushman, Darby & Cushman

[57] ABSTRACT

There are prepared acrylates and methacrylates of the formula

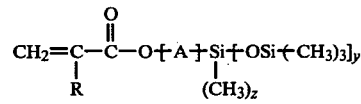

wherein R is hydrogen or methyl, y is 1 to 3, z is 0 to 2, y+z is 3, and wherein A is the unit (I)

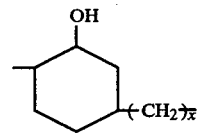

wherein x is 0 to 4, or the unit (II)

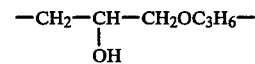

with the proviso that when A is unit II, then z is zero. The novel siloxane compounds can be copolymerized with (1) a monoethylenically unsaturated monomer having a polymerizable carbon-to-carbon double bond, and (2) a cross-linking agent having at least two polymerizable, ethylenically unsaturated bonds. The resulting copolymers have high oxygen permeability and proper hydrophilic property. They can be made substantially water non-absorptive. Contact lenses fabricated from such copolymers can, if desired, be worn continuously for long periods of time.

21 Claims, No Drawings

SILOXANE-CONTAINING POLYMERS AND CONTACT LENSES THEREFROM

BACKGROUND OF THE INVENTION

The present invention relates to a novel siloxane containing monomer, novel copolymers of that monomer, and the use of such copolymers in making contact lenses having high oxygen permeability.

Typical examples of known contact lenses developed with the object for continuous wear for a long term are silicone rubber contact lenses prepared from polydimethyl siloxane as a main component and high water content contact lenses prepared from poly-N-vinylpyrrolidone as a main component.

Since the silicone rubber contact lenses are very water-repellent and greatly different from cornea in thermal properties such as thermal conductivity and thermal diffusivity, they give a foreign body sensation, particularly a burning sensation despite having a large oxygen permeability. Therefore, there is required a strong patience to accommodate to the silicone rubber lenses. Further, the silicone rubber is so soft and elastic that they are subjected to precise mechanical treatments such as cutting, grinding, and polishing with difficulty. Also, many attempts for making the surface of silicone rubber lenses hydrophilic have been undertaken, but no completely satisfactory contact lens has been developed.

Since the high water content contact lenses contain about 60% to about 80% by weight of water, they have the disadvantages that (1) they are weaker in quality of material then low water content contact lenses, (2) they are easily contaminated with inorganic and organic compounds in tears which penetrate and accomulate into the lenses during the use, and (3) they are bad in maintenance of lens contour due to the evaporation of water during the use and, therefore, the refractive power thereof easily changes.

The most common soft contact lenses are prepared from poly(2-hydroxyethyl methacrylate) as a main component. In general, the water content of these contact lenses is usually of the order of 40% by weight and the oxygen permeability is insufficient. Therefore, these contact lenses have the defect that they cannot be worn continuously for as long a time as desired.

OBJECTS OF THE INVENTION

One or more of the following objects will be achieved by the practice of the invention.

An object of the invention is to develop a new silane monomer.

It is an object of the present invention to provide a novel copolymer suitable for use in contact lenses.

A further object of the invention is to provide a contact lens which can be continuously worn for a long term.

A still further object of the invention is to provide a contact lens which can be worn comfortably without giving a foreign body sensation and pain.

Another object of the invention is to provide siloxane-containing biocompatible contact lenses having a wide range of desirable optical properties, yet achieved with a minimum number of polymerizable comonomers.

Still another object of the invention is to provide a contact lens having an excellent oxygen permeability in spite of relatively low water content.

These and other objects of the invention will become apparent from the description hereinafter.

DETAILED DESCRIPTION

It has now been found that these objects can be attained by preparing novel acrylates and methacrylates of the formula

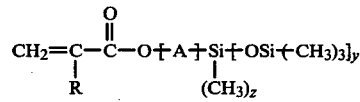

wherein R is hydrogen or methyl, y is 1 to 3, z is 0 to 2, y+z is 3, and wherein A is the unit (I)

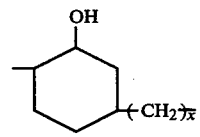

wherein x is 0 to 4, or the unit (II)

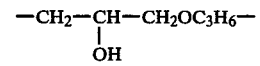

with the proviso that when A is unit II, then z is zero. The novel siloxane compounds can be copolymerized with (1) a monoethylenically unsaturated monomer having a polymerizable carbon-to-carbon double bond, in particular, with $C_1$-$C_8$alkyl 2-alkenoates and cyclo$C_5$-$C_7$alkyl 2-alkenoates, preferably $C_1$-$C_4$alkyl methacrylate or cyclohexyl methacrylate, and (2) a cross-linking agent having at least two polymerizable, ethylenically unsaturated bonds. The resulting novel copolymers have high oxygen permeability and proper hydrophilic property. They can be made substantially water non-absorptive. Contact lenses fabricated from such copolymers can, if desired, be worn continuously for long periods of time. In the practice of preferred embodiments of the invention the polymers have considerably higher $O_2$ permeability than is the case with normally high oxygen permeable siloxane-containing methacrylate polymers such as those disclosed in U.S. Pat. Nos. 4,139,513 and 4,139,692.

In the above formula when A is the divalent Unit (I), then R is preferably methyl, x is preferably 0 to 2, z is preferably 0, and y is preferably 3. When A is the divalent Unit (II), then R is preferably methyl, z is preferably zero, and y is preferably 3. It has been observed that the oxygen permeability of the novel contact lenses made from novel copolymers obtained in the practice of preferred embodiments of the invention is significantly higher, e.g., upwards to 100% and more, than the siloxane contact lenses of U.S. Pat. No. 4,235,985; see Table 3 of patent.

Illustrative subclasses of novel siloxane monomers include (3-hydroxy-4-methacryloyloxycyclohexyl)$C_1$-$C_4$alkyltris(trimethylsiloxy)silane, and (3-hydroxy-4-acryloyloxycyclohexyl)$C_1$-$C_4$alkyltris(trimethylsiloxy)silane.

Typical examples of novel monomers within the invention include:

2-hydroxy-4-[tris(trimethylsiloxy)silyl]cyclohexyl methacrylate,
2-hydroxy-4-[tris(trimethylsiloxy)silyl]cyclohexyl acrylate,
2-hydroxy-4-[bis(trimethylsiloxy)methylsilyl]cyclohexyl methacrylate,
2-hydroxy-4-[bis(trimethylsiloxy)methylsilyl]cyclohexyl acrylate,
2-hydroxy-4-[trimethylsiloxy)dimethylsilyl]cyclohexyl methacrylate,
2-hydroxy-4-[(trimethylsiloxy)dimethylsilyl]cyclohexyl acrylate,
$\beta$-(3-hydroxy-4-methacryloyloxycyclohexyl)ethyltris(trimethylsiloxy)silane,
$\beta$-(3-hydroxy-4-acryloyloxycyclohexyl)ethyltris(trimethylsiloxy)silane,
$\beta$-(3-hydroxy-4-methacryloyloxycyclohexyl)ethylbis(trimethylsiloxy)methylsilane,
$\beta$-(3-hydroxy-4-acryloyloxycyclohexyl)ethylbis(trimethylsiloxy)methylsilane,
$\beta$-(3-hydroxy-4-methacryloyloxycyclohexyl)ethyl(trimethylsiloxy)dimethylsilane,
$\beta$-(3-hydroxy-4-acryloyloxycyclohexyl)ethyl(trimethylsiloxy)dimethylsilane,
(3-hydroxy-4-methacryloyloxycyclohexyl)methyltris(trimethylsiloxy)silane,
(3-hydroxy-4-acryloyloxycyclohexyl)methyltris(trimethylsiloxy)silane,
(3-hydroxy-4-methacryloyloxycyclohexyl)methylbis(trimethylsiloxy)methylsilane,
(3-hydroxy-4-acryloyloxycyclohexyl)methylbis(trimethylsiloxy)methylsilane,
(3-hydroxy-4-methacryloyloxycyclohexyl)methyl(trimethylsiloxy)dimethylsilane,
(3-hydroxy-4-acryloyloxycyclohexyl)methyl(trimethylsiloxy)dimethylsilane,
$\gamma$-(3-hydroxy-4-methacryloyloxycyclohexyl)propyltris(trimethylsiloxy)silane,
$\gamma$-(3-hydroxy-4-acryloyloxycyclohexyl)propyltris(trimethylsiloxy)silane,
$\gamma$-(3-hydroxy-4-methacryloyloxycyclohexyl)propylbis(trimethylsiloxy)methylsilane,
$\delta$-(3-hydroxy-4-methacryloyloxycyclohexyl)butyl(tris(trimethylsiloxy)silane,
$\delta$-(3-hydroxy-4-acryloyloxycyclohexyl)butyltris(trimethylsiloxy)silane,
$\delta$-(3-hydroxy-4-methacryloyloxycyclohexyl)butylbis(trimethylsiloxy)methylsilane, and
$\epsilon$-[tris(trimethylsiloxy)silyl]propylglycerol methacrylate.

The novel monomeric siloxane compounds can be prepared, for example, by reacting the appropriate ethylenically unsaturated trimethoxysilane precursor with trimethylacetoxysilane, followed by epoxidation of the ethylenically unsaturated tris(trimethylsiloxy)silane with an appropriate epoxidation agent such as m-chloroperbenzoic acid, and thereafter reacting the resulting monoepoxy siloxane with an $\alpha,\beta$-ethylenically unsaturated monocarboxylic acid in the presence of a suitable catalyst and recovering the desired novel monomeric siloxane characterized within the scope of the above formula.

Illustrative of the trimethoxysilane precursors which can be employed are the following:
3-cyclohexenyltrimethoxysilane,
$\beta$-(3-cyclohexenyl)ethyltrimethoxysilane,
3-cyclohexenylmethyltrimethoxysilane,
$\gamma$-(3-cyclohexenyl)propyltrimethoxysilane,
$\delta$-(3-cyclohexenyl)butyltrimethoxysilane,
3-cyclohexenyl(methyl)dimethoxysilane,
$\beta$-(3-cyclohexenyl)ethyl(methyl)dimethoxysilane,
3-cyclohexenyl(dimethyl)methoxysilane,
$\beta$-(3-cyclohexenyl)ethyl(dimethyl)methoxysilane, and
($\gamma$-glycidoxypropyl)trimethoxysilane.

There are reacted three, two, or one moles of trimethylacetoxysilane with the trimethoxysilane precursor depending on whether there is to be formed a tris-, bis-, or mono-(trimethylsiloxy)silane product. An excess of the trimethylacetoxysilane can be employed. The reaction is normally carried out at ambient temperature, e.g., 20°–25° C.

While the presently preferred epoxidizing agent is m-chloroperbenzoic acid, there may be used other epoxidizing agents such as perbenzoic acid, peracetic acid, and performic acid.

As the catalyst for the reaction of the monoepoxysiloxane with, for example, methacrylic acid, there can be employed alkali metal hydroxides or alkaline earth metal hydroxides, e.g., potassium hydroxide. Other conventional catalysts for opening the epoxy group and for esterification may be employed. The esterification reaction is usually carried out with heating, e.g., to around 100° C. Preferably, the esterification reaction is carried out in the presence of a polymerization inhibitor, e.g., hydroquinone or hydroquinone monomethyl ether.

The novel copolymers comprise one or more of the siloxane monomers copolymerized with one or more of an alkyl 2-alkenoate or cycloalkyl 2-alkenoate and a relatively small amount of a cross-linking monomer. In general, novel copolymers containing from 20 to 80 parts by weight of the siloxane monomer and from 80 to 20 parts of the 2-alkenoate monomer having a wide spectrum of suitable properties can be prepared. In the practice of a highly preferred aspect of the invention the novel polymers contain about 30 to about 55 parts by weight of the siloxane monomer copolymerized with about 70 to about 45 parts by weight of a $C_1$–$C_4$alkyl methacrylate or acrylate, or a cyclohexyl methacrylate or acrylate, preferably with a small amount of a cross-linking monomer. Typical comonomers include methyl methacrylate, ethyl methacrylate, butyl methacrylate, 2-ethylhexyl methacrylate, cyclohexyl methacrylate, methyl acrylate, and the like.

The cross-linking agent may be present in an amount of up to 5% and higher, desirably from 0.1 to 3%, and preferably up to 2%, based on the total monomers. The cross-linking agent, including mixtures thereof, can be any of the conventional ethylenically unsaturated compounds containing at least two polymerizable ethylenic bonds. Thus, there can be used alkylene glycol and polyalkylene glycol esters of acrylic acid, methacrylic acid, or crotonic acid, e.g., ethylene glycol diacrylate, ethylene glycol dimethacrylate, propylene glycol diacrylate, propylene glycol dimethacrylate, 1,4-butylene glycol dimethacrylate, ethylene glycol dicrotonate, diethylene glycol dimethacrylate, diethylene glycol diacrylate, dipropylene glycol dimethacrylate, dipropylene glycol diacrylate, trimethylene glycol diacrylate, triethylene glycol diemthacrylate, triethylene glycol dicrotonate, tetraethylene glycol dimethacrylate, hexaethylene glycol dimethacrylate, tripropylene glycol diacrylate, tripropylene glycol dimethacrylate, tetrapropylene glycol dimethacrylate, tributylene glycol dimethacrylate, tetrabutylene glycol dimethacrylate, hexamethylene glycol dimethacrylate, octamethylene glycol dimethacrylate, and decamethylene glycol dimethacrylate. Other suitable cross-linking agents include allyl methacrylate, divinylbenzene, diallyl phthalate, trimethylolpropane trimethacrylate, diallyl tartrate, diallyl maleate, triallylmelamine, N,N'-methylenebisacrylamide, divinyl citraconate, diallyl fumarate, divinyl sulfone, triallyl phosphite, diallyl benzenephosphonate, hexahydro-1,3,5-triacryltriazine, divinyl ether, and triallyl citrate. Also useful as cross-linking agents are the polysiloxanyl-containing polyethylenically unsaturated compounds such as polysiloxanylbis(alkylglycerol acrylate) and polysiloxanylbis(alkylglycerol methacrylate) illustrated in U.S. Pat. No. 4,235,985, issued Nov. 25, 1980.

The high oxygen permeability of the novel copolymers is mainly due to its siloxane content. However, the greater the number of siloxane bonds in the novel polymer, the greater the tendency of an undesirable water-repellent characteristic developing in the polymer. In such an eventuality it may be desirable to include in the polymerization mixture a small amount of a hydrophilic monomer such as the hydroxyalkyl methacrylates and acrylates, e.g., 2-hydroethyl methacrylate; N-vinylpyrolidone; N,N-dimethylacrylamide; etc.

Polymerization can be carried out under conventional conditions. Thus, for example, polymerization can be carried out at 20° to 80° C., frequently 25°–45° C. The polymerization can be carried out employing a catalytically significant quantity of a free radical catalyst, e.g., from 0.05 to 1 percent based on the total weight of polymerizable monomers. Typical catalysts include t-butyl peroctoate, benzoyl peroxide, isopropyl percarbonate, 2,4-dichlorobenzoyl peroxide, methyl ethyl ketone peroxide, cumene hydroperoxide, and dicumyl peroxide. Additional free radical polymerization initiators which can be used include bis[4-(t-butylcyclohexyl]peroxydicarbonate, azobisisobutyronitrile, and azobisdimethylvaleronitrile. There can also be used irradiation by ultraviolet light, gamma rays, and high energy radiation, e.g., with cobalt 60.

The contact lenses of the invention can be prepared in conventional manner. For example, cast polymerization is suitable for preparing the novel contact lenses. Bulk polymerization may be conducted in a mold having the shape of a contact lens and the resulting molded lens may be subjected to a finishing step, e.g., buffing procedure, if desired. Also, the monomer mixture may be polymerized in an appropriate mold or vessel to give a block, sheet, or rod, and it may be then mechanically treated in a conventional manner to give a contact lens of a desired shape.

In the practice of preferred embodiments of the invention there are obtained novel hard contact lenses having excellent oxygen permeability, high optical qualities, transparency, inertness to bacteria and degradation under conventional contact lens cleaning and sterilization procedures, good mechanical properties, etc. The lenses are substantially water nonabsorptive and can be worn continuously for extended periods of time.

Unless otherwise indicated, all parts and percentages are by weight.

The process can comprise, consist essentially of, or consist of the stated steps with the materials set forth. The compositions can comprise, consist essentially of, or consist of the stated materials.

In the heading of the following Examples a number appears after both the reactant(s) employed and the product made therefrom. These numbers oftentimes are referred to in the text of the Examples.

The symbol "DK" represents oxygen permeability. The letter D represents the diffusion coefficient and K represents solubility. Oxygen permeability is expressed in the following units:

$$\frac{cm^3 - cm}{sec - cm^2 - cmHg} \times 10^{-10}$$

wherein $cm^3$ is the volume of oxygen, cm is the thickness of the polymer sample, sec. is the time, $cm^2$ is the area of the sample, cmHg is the driving force. The symbol "DK", as used herein, is the average of 3 oxygen permeability values.

EXAMPLE 1

Synthesis of 3-Cyclohexenyltris(trimethylsiloxy)silane (2) From 3-Cyclohexenyltrimethoxysilane (1) And Trimethylacetoxysilane.

To a 250 ml of three-necked round-bottomed flask equipped with a mechanical stirrer, a dropping funnel, and a thermometer there were added 30 grams (0.148 mole) of 3-cyclohexenyltrimethoxysilane and 64.7 grams (0.49 mole) of trimethylacetoxysilane. An ice-water bath was then placed under the reaction flask.

While the mixture was mechanically stirring, 10 grams of ethylsulfuric acid (prepared from 4.56 grams of concentrated sulfuric acid, 2.22 grams of absolute ethanol, and 3.22 grams of distilled water) were added dropwise, the temperature being maintained below 10° C. After the addition was complete, the mixture was continuously stirred at the same temperature for an additional 30 minutes, and the ice-water bath was removed. The stirring was continued at the ambient temperature, e.g., about 22° C. for 72 hours.

The mixture was poured into a 250 ml separatory funnel. Upon standing for 30 minutes, the separated acidic aqueous layer was removed. The top organic layer was washed with 3×50 ml of 5% sodium bicarbonate followed by 3×50 ml of distilled water. The washed organic layer was mixed with 150 ml of ether and dried over 100 grams of anhydrous sodium sulfate overnight. The hydrated sodium sulfate was filtered off, and the ether was removed from the filtrate under the rotovac at 40° C., and then under high vacuum (0.1–0.2 mm Hg) at room temperature overnight. The product yield was 57.2 grams. This product was dissolved in ether and passed through a chromatographic $Al_2O_3$ column. After evaporation of the ether, the yield of the purified product (2) was 40.3 grams, i.e., 72% based on (1). The purity of product (2) was 96.4% according to gas chromatographic analysis. The refractive index $n_D^{20}$ of the product was 1.4280. The infrared spectrum indicated the absorptions of Si—$(CH_3)_3$ at 1255 cm$^{-1}$, 840 cm$^{-1}$, and 750 cm$^{-1}$ space, of Si—O—Si at 1080–1040 cm$^{-1}$.

EXAMPLE 2

Synthesis of 3,4-Epoxycyclohexyltris(trimethylsiloxy)silane (3) From 3-Cyclohexenyltris(trimethylsiloxy)silane (2) And m-Chloroperbenzoic acid.

To a 2-liter three-necked round bottomed flask equipped with a mechanical stirrer and a condenser there were added 1 liter of methylene chloride and 140 grams of 80–85% technical grade of m-chloroperbenzoic acid, and the mixture was stirred at room temperature. To the resulting stirred mixture there were added 600 ml of methylene chloride solution containing 200 grams (0.531 mole) of 3-cyclohexenyltris(trimethylsiloxy)silane (2), dropwise, thus avoiding excessive foaming. After the addition was complete, the mixture was continuously stirred at room temperature for 20 hours. After the suspended solids were filtered off, the filtrate was washed with 5×150 ml of cold 5% NaHCO$_3$ solution followed by 5×100 ml of distilled water. The methylene chloride phase was dried over 150 grams of anhydrous sodium sulfate for three hours, then filtered. Removal of the methylene chloride from the filtrate was accomplished under 12–15 mm of Hg pressure and 35° C. There was obtained 205.6 grams of a yellow liquid product (3) with a purity of 95% according to gas chromatographic analysis.

Ten grams of product (3) were dissolved in 100 ml of hexane and stirred with 2 grams of charcoal for 30 minutes. The hexane solution was filtered through celite. After thorough removal of hexane under aspirator pressure (12–15 mm of Hg) at 35° C., the colorless liquid product gave the following properties. Purity in GC: 98.81%; $n_D^{20}$: 1.4354; the infrared spectrum of (3) shows disappearance of CH stretching frequency at the unsaturated C=C bond at 3025 cm$^{-1}$ and appearance of the absorption of the epoxy ring vibration at 835 cm$^{-1}$. Absorption band of Si(CH$_3$)$_3$ at 1225 cm$^{-1}$ has not been changed.

EXAMPLE 3

Synthesis of 2-Hydroxy-4-tris(trimethylsiloxy)silylcyclohexyl methacrylate (4) from 3,4-Epoxycyclohexyltris(trimethylsiloxy)silane (3) and Methacrylic Acid.

One hundred ninety six grams (0.499 mole) of 3,4-epoxycyclohexyltris(trimethylsiloxy)silane (3) were added to a 500 ml three-necked round-bottomed flask equipped with a condenser and a mechanical stirrer, and while stirring, 3.2 grams of crushed technical grade KOH and 0.4 gram (0.0364 mole) of hydroquinone were added. To the mixture, 86 grams (1 mole) of methacrylic acid were added dropwise at room temperature. After the addition of the methacrylic acid was complete, the reaction flask was immersed in an oil bath which was gradually heated up to 95°–100° C. The heating was continued at that temperature for 9 hours followed by stirring at room temperature overnight.

The resulting reaction mixture was added to 600 ml of hexane, followed by filtering the solids therefrom. The filtrate was washed with 4×150 ml of 5% NaOH solution followed by 6×100 ml of 10% NaCl solution wash. The recovered hexane solution was dried over 200 grams of granular anhydrous sodium sulfate. The dried hexane solution was further decolorized with 4×10 grams of charcoal. After the removal of hexane at the aspirator pressure and under the reduced pressure of 0.1 mm Hg, the product (4) was an extremely viscous, pale yellow liquid. Gas chromatographic analysis indicated that product (4) was a mixture of two isomers, and the refractive index $n_D^{20}$ of (4) was 1.4452. Infrared spectrum showed absorption bands of OH at 3450 cm$^{-1}$, of two carbonyl groups at 1723 cm$^{-1}$ and 1705 cm$^{-1}$, of C=C at 1642 cm$^{-1}$, of Si(CH$_3$)$_3$ at 1255 cm$^{-1}$ and 840 cm$^{-1}$, of C—O stretching of ester group at 1170 cm$^{-1}$, of Si—O—Si at 1080–1040 cm$^{-1}$.

The following is the elemental analysis for 2-hydroxy-4-tris(trimethylsiloxy)silylcyclohexyl methacrylate (4):
Calculated for C$_{19}$H$_{42}$O$_6$Si$_4$: C 47.65%; H 8.84%; Found: C 47.50%; H 8.66%.

EXAMPLE 4

Synthesis of β-(3-Cyclohexenyl)ethyltris(trimethylsiloxy)silane (6) From β-(3-Cyclohexenyl)-ethyltrimethoxysilane (5) And Trimethylacetoxysilane.

Two hundred grams (0.868 mole) of β-(3-cyclohexenyl)ethyltrimethoxysilane (5) and 392.4 grams (2.97 mole) of trimethylacetoxysilane were mixed in a 1000 ml three-necked round-bottomed flask equipped with a mechanical stirrer, a dropping funnel, and a thermometer. While the mixture was stirring in an ice-water bath maintained at 0° C.–10° C., 64.5 grams of ethylsulfuric acid prepared as before were added dropwise during one hour period. Stirring was continued for an additional 30 minutes at 0° C.–10° C. followed by 72 hours of stirring at room temperature. The mixture was then transferred to a one-liter separatory funnel. The aqueous layer was removed, and the top organic layer was washed with 2×100 ml of 5% NaHCO$_3$ solution followed by 2×100 ml of 10% NaCl solution. The separated organic layer was dried over 150 grams of anhydrous sodium sulfate overnight. The yield of the pale yellow liquid was 350.3 grams (95% pure). Five grams of this liquid (6) was mixed with diethyl ether and charcoal, and the resulting admixture was passed through a chromatographic column. There were obtained 3.5 grams of colorless, viscous liquid. Gas chromatographic analysis indicated that the purity was 99.6% and that the refractive index $n_D^{20}$ of product (6) was 1.4313. The infrared spectrum showed absorption bands of C—H at double bond at 3050 cm$^{-1}$, of Si—(CH$_3$)$_3$ at 1255 cm$^{-1}$ and 840 cm$^{-1}$, of Si—O—Si at 1080–1040$^{-1}$ cm.

EXAMPLE 5

Synthesis of β-(3,4-Epoxycyclohexyl)ethyltris(trimethylsiloxy)silane (7) From β-(3,4-Cyclohexenyl)ethyltris(trimethylsiloxy)silane (6) And m-Chloroperbenzoic acid.

Three hundred fifty grams (0.865 mole) of unpurified β-(3,4-cyclohexenyl)ethyltris(trimethylsiloxy)-silane obtained from the reaction in Example 4 were slowly added to a 5 liter three-necked round-bottomed flask containing the stirring mixture of 2 liters of methylene chloride and 184 grams of m-ClC$_6$H$_4$CO$_3$H at room temperature, in order to avoid excessive heat and foaming. After the addition was complete, the reaction mixture was stirred overnight at room temperature. Methylene chloride was stripped from the mixture, and the remainder was kept in the freezer for 4 hours to precipitate the solids. After filtration, there was obtained 200 grams of a yellow viscous filtrate with a purity of 96.4%.

In order to obtain the colorless liquid product (7), 3 grams of the yellow filtrate were mixed with 100 ml of anhydrous ether and 1 gram of charcoal, and stirred for 2 hours at ambient temperature. The solution was passed through celite followed by thorough removal of ether under vacuum. The pale yellow viscous liquid (7) obtained had a purity of 96.4% according to gas chromatographic analysis; refractive index $n_D^{20}$ of 1.4336. Infrared spectrum of (7) showed that C—H stretching of H—C=C at 3050 cm$^{-1}$ was disappeared due to the oxidation of the double bond to the epoxide. Peaks at 1250 cm$^{-1}$ and 835 cm$^{-1}$ for Si—(CH$_3$)$_3$, at 1080–1040 cm$^{-1}$ of Si—O—Si, proved that these groups remained intact to the rest of the molecule.

EXAMPLE 6

Synthesis of β-(3-Hydroxy-4-methacryloyloxycyclohexyl)ethyltris(trimethylsiloxy)silane (8) From β-(3,4-Epoxycyclohexyl)ethyltris(trimethylsiloxy)silane (7) And Methacrylic Acid.

Forty two grams (0.1 mole) of β-(3,4-epoxycyclohexyl)ethyltris(trimethylsiloxy)silane were mixed with 1.0 gram of hydroquinone and stirred in a 100 ml three-necked round-bottomed flask equipped with a mechanical stirrer, dropping funnel, and a condenser. To the stirring mixture there were added 17.2 grams (0.2 mole) of methacrylic acid dropwise in 30 minutes at room temperature. The mixture was then heated up to 95°–100° C. in an oil bath and slowly refluxed for 8–9 hours followed by stirring at room temperature for 2–3 hours.

The mixture was mixed with 250 ml of hexane. The solids were removed by filtration, and the filtrate was washed with 2×50 ml of 5% NaOH solution followed by 7×50 ml of 10% NaCl solution. The organic layer was then dried over 75 grams of anhydrous sodium sulfate. The product (8) was 43.3 grams. The yellow liquid product was mixed with 300 ml of ether and 10 grams of charcoal and stirred for 3½ hours to further decolorize the product. Final purification was accomplished by passing the product-ether-charcoal mixture through the chromatographic Al$_2$O$_3$ column. After evaporation of the ether, the pale yellow liquid product (8) had a refractive index n$_D^{20}$ of 1.4465 and purity of 96.2% according to gas chromatographic analysis. Infrared spectrum showed absorption bands of OH at 3550 cm$^{-1}$, of two C=O groups at 1730 cm$^{-1}$ and 1715 cm$^{-1}$ for the two isomers, of C=C at 1645 cm$^{-1}$, of Si(CH$_3$)$_3$ at 1255 cm$^{-1}$ and 840 cm$^{-1}$, C—O stretching band of ester at 1180 cm$^{-1}$, of Si—O—Si at 1080–1040 cm$^{-1}$.

The following is the result of the elemental analysis of β-(3-hydroxy-4-methacryloyloxycyclohexyl)ethyltris(trimethylsiloxy)silane (8):

Calculated for C$_{21}$H$_{46}$O$_6$Si$_4$: C 49.75%; H 9.15%; Found: C 49.21%; H 8.85%.

EXAMPLE 7

Copolymerization of 2-Hydroxy-4-tris(trimethylsiloxy)silylcyclohexyl Methacrylate (4) with Methyl Methacrylate.

(a) Eight grams of 2-hydroxy-4-tris(trimethylsiloxy)silylcyclohexyl methacrylate (4), 11.6 grams of methyl methacrylate, 0.4 gram of ethylene glycol dimethacrylate, and 0.04 gram of bis[4-t-butylcyclohexyl]peroxydicarbonate were mixed together, degassed, and polymerized in closed polypropylene syringes in an oven at 30° C. for 24 hours. Then the temperature was raised to 115° C. and kept at that temperature for 2 hours. The syringes were taken out and the polymer cut to optical buttons. The optical buttons were heated at 120° C. for 1 hour in the oven and cooled to room temperature with the cooling rate of 0.16° C./min. The optical buttons obtained in this way were slightly hazy, but hard enough to lathe cut and polished to clear and transparent contact lenses. Oxygen permeability measured by Mandell, see using a Schema Versatae Oxygen Flux Meter in a controlled temperature of 25° C. was 11.1 in terms of the permeability unit, $\overline{DK}$, as defined by Fatt I, Polarographic Oxygen Sensors, Cleveland, CRC Press, 1976, p. 128.

(b) Eleven grams of 2-hydroxy-4-tris(trimethylsiloxy)silylcyclohexyl methacrylate (4), 8.6 grams of methyl methacrylate, 0.4 gram of ethylene glycol dimethacrylate, and 0.04 gram of bis[4-t-butylcyclohexyl]peroxydicarbonate were mixed together, degassed, and polymerized in the polypropylene syringes in the oven at 30° C. for 24 hours. The temperature of the oven was raised to 115° C. where the polymerized material was kept for 2 hours. After the syringes were taken out, the polymer was cut to form optical buttons. The buttons were heated at 120° C. for 1 hour and slowly annealed to room temperature with the cooling rate of 0.16° C./min. The optical buttons obtained were hard and slightly hazy, but contact lenses made from the buttons were clear and transparent. Oxygen permeability measured as above had a $\overline{DK}$ value of 26.4 at 25° C. in the dry state.

EXAMPLE 8

Copolymerization of β-(3-hydroxy-4-methacryloyloxycyclohexyl)ethyltris(trimethylsiloxy)silane (8) with Methyl Methacrylate.

(a) Ten grams of β-(2-hydroxy-3-methacryloyloxycyclohexyl)ethyltris(trimethylsiloxy)silane (8) were mixed with 14.50 grams of methyl methacrylate, 0.5 gram of bis[4-t-butylcyclohexyl]peroxydicarbonate and stirring for 10 minutes until the solution became homogeneous. The mixture was degassed, poured into the polypropylene syringes and polymerized at 30° C. for 24 hours in the oven. The oven temperature was raised to 115° C. and kept for 2 hours at that temperature. The polymerized material was taken out and cut to form hard and transparent optical buttons, which were then heated at 115° C. for 1 hour and cooled to room temperature with the cooling rate of 0.16° C./minute. The buttons were lathe cut and polished to contact lenses with good focus. The oxygen permeability of the lenses thus prepared was measured as described above and the $\overline{DK}$ was 11.1 at 25° C.

(b) Eleven grams of β-(3-hydroxy-4-methacryloyloxycyclohexyl)ethyltris(trimethylsiloxy)silane (8) were mixed with 8.6 grams of methyl methacrylate, 0.4 gram of bis[4-t-butylcyclohexyl]peroxydicarbonate and stirred for 5 minutes. After the mixture was degassed, it was poured in the polypropylene syringes and the syringes closed tight. The syringes were kept in the oven maintained at 30° C. for 24 hours. The syringes were then heated at 115° C. for 2 hours. The syringes were taken out, cut, and hard and transparent optical buttons were obtained and then heated again at 115° C. for 1 hour and slowly cooled to room temperature with the cooling rate of 0.16° C./minute. The optical buttons were lathe cut and polished to contact lenses with good focus. Oxygen permeability $\overline{DK}$ measured at 25° C. by Mandell was 28.4.

EXAMPLE 9

Synthesis of Tris(trimethylsiloxy)propoxypropylene Oxide (11) from (γ-Glycidoxypropyl)trimethoxysilane (10) and Trimethylacetoxysilane.

To a three-necked three-liter round-bottomed flask equipped with a thermometer, a mechanical stirrer, and a dropping funnel, there were added 472.6 g (2.0 moles) of (γ-glycidoxypropyl)trimethoxysilane (10) and 872.5 g (6.61 moles) of trimethylacetoxysilane under mechanical stirring in an ice-water bath maintained at 5°–10° C. Two hundred fifty grams (250 g) of distilled water were added dropwise to the stirring mixture over a period of 90 minutes. After the addition of the distilled water was complete, the mixture was then vigorously stirred for 72 hours at ambient temperature. The mixture was transferred to a five liter separatory funnel. After the two layers were clearly separated, the aqueous bottom layer was removed, and the organic top layer was dried over 150 g of anhydrous $Na_2SO_4$ for a few hours. The solids were removed by filtration, and the filtrate was placed under the vacuum at 0.1 mm Hg and 40° C. for 3 hrs. to remove lower volatiles including trimethylacetoxysilane and water. A 100 ml ether wash was used to remove $Na_2SO_4$. The residue (10) was 489.3 g and the purity was 82% according to gas chromatographic analysis. The impure epoxide (10) was further purified using acetone and chromatographic $Al_2O_3$. Epoxide product (11), 243.6 g, having a purity of 90% was obtained. Repurification of epoxide (11) as above followed by thorough removal of the acetone gave epoxide (11) with purity of 99.5%. Its infrared spectrum is consistent with the assigned structure. The refractive index $n_D^{20}$ of tris(trimethylsiloxy)silylpropoxypropylene oxide (11) was 1.4196.

EXAMPLE 10

Synthesis of Tris(trimethylsiloxy)silylpropylglycerol Methacrylate (12) From Tris(trimethylsiloxy)silylpropoxypropylene Oxide (11) and Methacrylic Acid.

To 153.4 g of 90% tris(trimethylsiloxy)silylpropoxypropylene oxide (11), 3.74 g of crushed KOH, and $5 \times 10^{-2}$ g of hydroquinone contained in a 500 ml, three-necked, round-bottomed flask equipped with a cooling condenser, a mechanical stirrer, and a dropping funnel, there were added 112.7 g (1.31 moles) of methacrylic acid dropwise in over a period of 20 minutes. After the addition was complete, the reaction flask was immersed in an oil-bath and heated to 95° C.–100° C. for 9 hrs. The reaction mixture was cooled to room temperature. To this mixture, 300 ml of ether were added, and solids were filtered therefrom. The ether solution was washed with $4 \times 75$ ml of 10% NaOH solution followed by $3 \times 100$ ml of 5% $Na_2SO_4$ solution. The resulting aqueous layer was removed; the upper ether layer (solution) was dried over 120 g of anhydrous $Na_2SO_4$ overnight. After purification using a column packed with chromatographic $Al_2O_3$ and ether, 132.1 g of pale yellow liquid (12) having a purity of 96.5% was obtained. Repurification of this liquid with the $Al_2O_3$ and charcoal gave a liquid (12) of 99.2% purity. The refractive index $n_D^{20}$ of product (12) was 1.4324. Its infrared spectra indicated absorption bands of OH at 3480 cm$^{-1}$, of C=O at 1723 cm$^{-1}$, of C=C at 1640 cm$^{-1}$, of $Si(CH_3)_3$ at 1250 cm$^{-1}$ and 840 cm$^{-1}$, of C—O stretching band of ester at 1180 cm$^{-1}$ and of Si—O—Si at 1100–1030 cm$^{-1}$.

Elemental analysis of (12) is shown below:
Calculated for $C_{19}H_{44}O_7Si_4$: C 45.93%; H 8.92%; Found: C 45.8%; H 8.84%.

EXAMPLE 11

Copolymerization of Tris(trimethylsiloxy)silylpropylglycerol Methacrylate (12) with Methyl Methacrylate.

(a) Twelve grams of tris(trimethylsiloxy)silylpropylglycerol methacrylate (12), 1.2 g of methacrylic acid, 16.2 g of methyl methacrylate, and 0.6 g of ethylene glycol dimethacrylate were mixed together, and stirred for ten minutes in a 150 ml Erlenmeyer flask. To this mixture was added 0.06 g of 2,2'-azobis(2,4-dimethyl-4-methoxyvaleronitrile), under stirring, until a homogeneous mixture was obtained. This liquid mixture was poured into polypropylene test tubes and maintained under a nitrogen atmosphere for 3–5 minutes and capped with low density polyethylene caps. Polymerization was effected in a water-bath at 30° C. for 24 hours. The test tubes were removed from the water-bath, cut into clear transparent optical buttons which were heated to 124° C. for 80 minutes under $N_2$ atmosphere and then slowly cooled to room temperature at a cooling rate of 0.2° C./min. The optical buttons were lathe cut and polished to hard contact lenses.

(b) Sixteen and a half grams (16.5 g) of tris(trimethylsiloxy)silylpropylglycerol methacryalte, 0.6 g of ethylene glycol dimethacrylate, and 0.06 g of 2,2'-azobis(2,4-dimethyl-4-methoxyvaleronitrile) were added to a 150 ml Erlenmeyer flask and stirred until a homogeneous solution was obtained. The liquid mixture was poured into polypropylene test tubes and maintained under a $N_2$ atmosphere for 3–5 minutes. The test tubes were then capped as above and polymerized at 30° C. for 24 hrs. in the water bath. The test tubes were cut and transparent optical buttons were heated at 124° C. for 80 minutes under a nitrogen atmosphere and annealed to room temperature at a cooling rate of 0.2° C./minute. The buttons were lathe cut and polished to contact lenses.

EXAMPLES 12–17

Following the procedure set forth in Example 7 (a) and (b), various polymers and contact lens therefrom were prepared using varying amounts of 2-hydroxy-4-tris(trimethylsiloxy)silylcyclohexyl methacrylate, methyl methacrylate, ethylene glycol dimethacrylate, and bis[4-t-butylcyclohexyl]peroxydicarbonate. The pertinent data are set forth in Table I below.

TABLE I

| Example | Si[1] % | MMA[2] % | EGDMA[3] % | P-16[4] | $\bar{n}_D^{25[5]}$ | $\overline{DK}^{[6]}$ |
|---|---|---|---|---|---|---|
| 12 | 30 | 68 | 2 | 0.2 | 1.4786 | 3.6 |
| 13 | 35 | 63 | 2 | 0.2 | 1.4787 | 8.5 |
| 14 | 40 | 58 | 2 | 0.2 | 1.4766 | 11.1 |
| 15 | 45 | 53 | 2 | 0.2 | 1.4738 | 15.4 |
| 16 | 50 | 48 | 2 | 0.2 | 1.4675 | 20.5 |
| 17 | 55 | 43 | 2 | 0.2 | 1.4693 | 26.4 |

[1] 2-Hydroxy-4-tris(trimethylsiloxy)silylcyclohexyl methacrylate
[2] Methyl Methacrylate
[3] Ethylene glycol dimethacrylate
[4] bis[4-t-butylcyclohexyl]peroxydicarbonate
[5] Index of refraction of optical button; $\bar{n}_D^{25}$ represents average value of both surfaces.
[6] $O_2$ permeability; average of 3 measurements; $\overline{DK}$ value $\times 10^{-10}$ ($cm^3$-cm/sec-$cm^2$-cmHg). See Example 7 (a).

EXAMPLES 18–23

Following the procedure set forth in Example 8 (a) and (b), various polymers and contact lens therefrom were prepared using varying amounts of β-(3-hydroxy-4-methacryloyloxycyclohexyl)ethyltris(trimethylsiloxy)silane, methyl methacrylate, ethylene glycol dimethacrylate, and bis[4-t-butylcyclohexyl]peroxydicarbonate. The pertinent data are set forth in Table II below.

TABLE II

| Example | Si[1] % | MMA[2] % | EGDMA[3] % | P-16[4] | $\bar{n}_D^{25[5]}$ | $\overline{DK}^{[6]}$ |
|---|---|---|---|---|---|---|
| 18 | 30 | 68 | 2 | 0.2 | 1.4859 | 3.8 |

TABLE II-continued

| Example | Si(1) % | MMA(2) % | EGDMA(3) % | P-16(4) | $\bar{n}_D^{25(5)}$ | $\overline{DK}^{(6)}$ |
|---|---|---|---|---|---|---|
| 19 | 35 | 63 | 2 | 0.2 | 1.4753 | 9.6 |
| 20 | 40 | 58 | 2 | 0.2 | 1.4768 | 11.1 |
| 21 | 45 | 53 | 2 | 0.2 | 1.4774 | 15.9 |
| 22 | 50 | 48 | 2 | 0.2 | 1.4716 | 21.1 |
| 23 | 55 | 43 | 2 | 0.2 | 1.4668 | 28.4 |

(1)β-(3-hydroxy-4-methacryloyloxycyclohexyl)ethyltris(trimethylsiloxy)silane
(2)Methyl Methacrylate
(3)Ethylene glycol dimethacrylate
(4)bis[4-t-butylcyclohexyl]peroxydicarbonate
(5)Index of refraction of optical button; $\bar{n}_D^{25}$ represents average value of both surfaces.
(6)O₂ permeability; average of 3 measurements; $\overline{DK}$ value × 10⁻¹⁰ (cm³-cm/sec-cm²-cmHg). See Example 7(a).

EXAMPLES 24–29

Following the procedure set forth in Example 11 (a) and (b), various polymers and contact lens therefrom were prepared using varying amounts of tris(trimethylsiloxy)silylpropylglycerol methacrylate, methyl methacrylate, methacrylic acid, ethylene glycol dimethacrylate, and 2,2'-azobis(2,4-dimethyl-4-methoxyvaleronitrile). The pertinent data are set forth in Table III below.

TABLE III

| Example | Si(1) % | MMA(2) % | EGDMA(3) % | MA(4) | A20(5) | $\bar{n}_D^{25(6)}$ |
|---|---|---|---|---|---|---|
| 24 | 30 | 64 | 2 | 4 | 0.2 | 1.4833 |
| 25 | 35 | 59 | 2 | 4 | 0.2 | 1.4795 |
| 26 | 40 | 54 | 2 | 4 | 0.2 | 1.4770 |
| 27 | 45 | 49 | 2 | 4 | 0.2 | 1.4748 |
| 28 | 50 | 44 | 2 | 4 | 0.2 | 1.4754 |
| 29 | 55 | 39 | 2 | 4 | 0.2 | 1.4723 |

(1)Tris(trimethylsiloxy)silylpropylglycerol methacrylate.
(2)Methyl Methacrylate
(3)Ethylene glycol dimethacrylate
(4)Methacrylic acid
(5)2,2'-Azobis(2,4-dimethyl-4-methoxyvaleronitrile)
(6)Index of refraction of optical button; $\bar{n}_D^{25}$ represents average value of both surfaces.

The contact lenses made in the preceding examples exhibit high oxygen permeability, substantially water-nonabsorptive but proper hydrophilicity, excellent optical characteristics, transparency, and can be comfortably worn continuously for a long period of time. Optical buttons of the polymers exhibited good processing characteristics, i.e., they are sufficiently hard and can be readily cut and polished using conventional techniques into the shape of commercial contact lenses having excellent optical qualities.

What is claimed is:

1. An organosiloxane of the formula

wherein R is hydrogen or methyl, and wherein A is the unit (I)

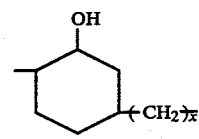

wherein x is 0 to 4

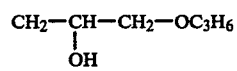

2. An acrylate or methacrylate according to claim 1 wherein x is 0 to 2.

3. An acrylate or methacrylate according to claim 2 wherein R is methyl.

4. A methacrylate according to claim 3 wherein x is 0.

5. A methacrylate according to claim 3 wherein x is 2.

6. A methacrylate according to claim 2 wherein R is methyl.

7. A copolymer of (1) 20 to 80% of an organosilane of claim 1 and (2) the balance a mixture consisting essentially of (a) an ester of the group consisting of alkyl acrylte, alkyl methacrylate, cyclohexyl acrylate, and cyclohexyl methacrylate, and (b) a polyethylenically unsaturated cross-linking agent, the cross-linking agent being present in an amount up to 5% of the total weight of the copolymerizable monomers.

8. A copolymer according to claim 7 wherein said ester is a $C_1$–$C_4$-alkyl methacrylate and wherein the organosilane represents 30 to 55% of the copolymer.

9. A copolymer according to claim 8 wherein the ester is methyl methacrylate.

10. A copolymer according to claim 8 wherein x is 0 to 2.

11. A copolymer according to claim 9 wherein R is methyl.

12. A copolymer according to claim 10 wherein x is 0.

13. A contact lens made of the copolymer of claim 8.
14. A contact lens made of the copolymer of claim 9.
15. A contact lens made of the copolymer of claim 10.
16. A contact lens made of the copolymer of claim 11.
17. A contact lens made of the copolymer of claim 12.

18. A process of preparing compounds of claim 1 comprising (1) reacting a compound of the formula (I)

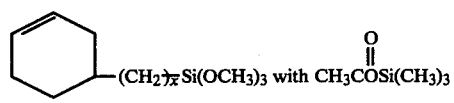

under acidic conditions to form a compound of the formula II

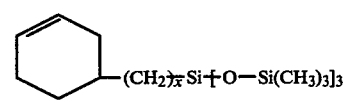

(2) reacting the thus formed compound (II) with an epoxidizing compound capable of epoxidizing the double bond in the cyclohexene ring to form a compound of the formula (III)

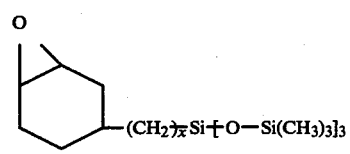

(3) reacting the compound of formula (III) with a compound of the formula

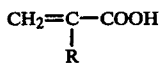

in the presence of an esterification catalyst to form the compounds of claim 1.

19. A process of preparing the copolymer of claim 10 comprising reacting (1), 2(a), and 2(b) in the presence of a free radical polymerization initiator.

20. A process of preparing a contact lens comprising carrying out the polymerization of claim 19 in bulk, cutting the copolymer to form optical buttons, and mechanically forming the optical buttons into contact lenses.

21. The process of claim 20 in which the copolymer of claim 8 is formed into said contact lenses.

* * * * *